US007835868B2

(12) United States Patent
Richard et al.

(10) Patent No.: US 7,835,868 B2
(45) Date of Patent: Nov. 16, 2010

(54) PROCESS FOR SELECTING SHAPED PARTICLES FOR USE IN A PACKED BED

(75) Inventors: Michael Alan Richard, Fulshear, TX (US); Paul Michael McAllister, Houston, TX (US); Anne Taylor Coleman, Richmond, TX (US); Johannes Leopold Marie Syrier, Houston, TX (US); Alouisius Nicolaas Renée Bos, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1402 days.

(21) Appl. No.: 11/232,353

(22) Filed: Sep. 21, 2005

(65) Prior Publication Data

US 2006/0065064 A1 Mar. 30, 2006

Related U.S. Application Data

(60) Provisional application No. 60/612,696, filed on Sep. 24, 2004.

(51) Int. Cl.
*G01N 33/48* (2006.01)
*G06G 7/58* (2006.01)
*B01J 23/48* (2006.01)

(52) U.S. Cl. .............................. 702/19; 702/20; 703/11; 703/12; 502/347

(58) Field of Classification Search ................. None
See application file for complete search history.

(56) References Cited

U.S. PATENT DOCUMENTS

| | | | | |
|---|---|---|---|---|
| 2,238,474 A | 4/1941 | McNamee | ................... | 260/348 |
| 2,424,083 A | 7/1947 | Finch | .......................... | 252/204 |
| 2,901,441 A | 8/1959 | Waterman | ................... | 252/463 |
| 3,563,913 A | 2/1971 | de Krijger et al. | ............ | 252/463 |
| 3,563,914 A | 2/1971 | Wattimena | ................... | 252/463 |
| 3,844,981 A | 10/1974 | Cusumano | ................... | 252/471 |
| 3,895,093 A | 7/1975 | Weidenbach et al. | ...... | 423/213.5 |
| 3,937,476 A | 2/1976 | Sakai | ........................ | 274/39 A |
| 3,962,136 A | 6/1976 | Nielsen et al. | ............... | 252/454 |
| 3,962,285 A | 6/1976 | Cusumano | ............ | 260/348.5 R |
| 3,972,829 A | 8/1976 | Michalko | ..................... | 252/430 |
| 3,997,476 A | 12/1976 | Cull | ........................... | 252/463 |
| 4,005,049 A | 1/1977 | Fields | ........................ | 252/467 |
| 4,033,903 A | 7/1977 | Maxwell | ..................... | 252/476 |
| 4,125,480 A | 11/1978 | Maxwell | ..................... | 252/414 |
| 4,186,106 A | 1/1980 | Rebsdat et al. | ............... | 252/414 |
| 4,207,210 A | 6/1980 | Kilty | ........................... | 252/463 |
| 4,212,772 A | 7/1980 | Mross et al. | ................. | 252/476 |
| 4,235,798 A | 11/1980 | Bartley et al. | ........... | 260/449 R |
| 4,244,889 A | 1/1981 | Bartley et al. | ............... | 564/132 |
| 4,356,312 A | 10/1982 | Nielsen et al. | ............... | 549/534 |
| 4,358,623 A | 11/1982 | Murphy et al. | ............... | 568/473 |
| 4,361,500 A | 11/1982 | Mathe et al. | ................. | 252/430 |
| 4,361,503 A | 11/1982 | Dwyer et al. | ............ | 252/455 Z |
| 4,361,504 A | 11/1982 | Solomon et al. | ............ | 252/463 |
| 4,366,092 A | 12/1982 | Winterton | ................... | 252/476 |
| 4,366,093 A | 12/1982 | Shiozaki et al. | ......... | 252/477 R |
| 4,367,167 A | 1/1983 | Lee et al. | ..................... | 252/472 |
| 4,368,144 A | 1/1983 | Mitsuhata et al. | ........... | 252/463 |
| 4,379,134 A | 4/1983 | Weber et al. | ................. | 423/626 |
| 4,382,149 A | 5/1983 | Krueger | ....................... | 568/473 |
| 4,420,420 A | 12/1983 | Mita et al. | ................... | 502/261 |
| 4,458,032 A | 7/1984 | Rebsdat et al. | .............. | 502/348 |
| 4,471,071 A | 9/1984 | Rebsdat et al. | .............. | 502/347 |
| 4,511,671 A | 4/1985 | Saito et al. | ................... | 502/242 |
| 4,532,231 A | 7/1985 | Johnson | ...................... | 502/347 |
| 4,628,129 A | 12/1986 | Bartley | ....................... | 568/864 |
| 4,645,754 A | 2/1987 | Tamura et al. | .............. | 502/527 |
| 4,656,157 A | 4/1987 | Hofmann et al. | ............ | 502/439 |
| 4,665,048 A | 5/1987 | Van Leeuwen et al. | ...... | 502/221 |
| 4,728,634 A | 3/1988 | Boxhoorn et al. | ........... | 502/243 |
| 4,731,350 A | 3/1988 | Boxhoorn et al. | ........... | 502/231 |
| 4,761,394 A | 8/1988 | Lauritzen | .................... | 502/348 |
| 4,766,105 A | 8/1988 | Lauritzen | .................... | 502/216 |
| 4,797,270 A | 1/1989 | Alvarado Cendan et al. | ..... | 423/625 |
| 4,797,279 A | 1/1989 | Karamata et al. | ............. | 424/93 |
| 4,808,738 A | 2/1989 | Lauritzen | .................... | 549/536 |

(Continued)

FOREIGN PATENT DOCUMENTS

CN 85109109 4/1987

(Continued)

OTHER PUBLICATIONS

R. Byron Bird et al., "Transport Phenomena," 1960 J. Wiley & Sons, pp. 198-201.

(Continued)

*Primary Examiner*—Shubo (Joe) Zhou

(57) ABSTRACT

A process for selecting shaped particles for use in a tube which is capable of being packed with shaped particles to form a packed bed in the tube. A desired value of one or more properties of the packed bed is defined. The dimensions of the shaped particles are calculated such that a packed bed in the tube of the shaped particles having the calculated dimensions meets or substantially meets the desired value(s), and shaped particles are selected in accordance with the calculated dimensions. The properties of the packed bed may be the volume fraction which is occupied by shaped particles, the packing density, and the resistivity for a gas flowing through the packed bed.

10 Claims, 2 Drawing Sheets

U.S. PATENT DOCUMENTS

| | | | | |
|---|---|---|---|---|
| 4,810,689 A | 3/1989 | Hayden | | 502/347 |
| 4,820,675 A | 4/1989 | Lauritzen | | 502/216 |
| 4,829,044 A | 5/1989 | Boxhoorn et al. | | 502/348 |
| 4,837,194 A | 6/1989 | Hayden | | 502/348 |
| 4,845,296 A | 7/1989 | Ahmed et al. | | 564/477 |
| 4,874,739 A | 10/1989 | Boxhoorn | | 502/218 |
| 4,886,917 A | 12/1989 | Knopf et al. | | 568/623 |
| 4,908,343 A | 3/1990 | Bhasin | | 502/218 |
| 4,916,243 A | 4/1990 | Bhasin et al. | | 549/534 |
| 4,921,681 A | 5/1990 | Ozero et al. | | 422/197 |
| 4,939,114 A | 7/1990 | Nojiri et al. | | 502/348 |
| 4,994,587 A | 2/1991 | Notermann et al. | | 549/534 |
| 4,994,588 A | 2/1991 | Kapicak et al. | | 549/534 |
| 4,994,589 A | 2/1991 | Notermann | | 549/534 |
| 5,037,794 A | 8/1991 | Magistro | | 502/355 |
| 5,055,442 A | 10/1991 | Osaka et al. | | 502/439 |
| 5,057,481 A | 10/1991 | Bhasin | | 502/208 |
| 5,100,859 A | 3/1992 | Gerdes et al. | | 502/439 |
| 5,112,795 A | 5/1992 | Minahan et al. | | 502/324 |
| 5,145,824 A | 9/1992 | Buffum et al. | | 502/216 |
| 5,187,140 A | 2/1993 | Thorsteinson et al. | | 502/348 |
| 5,254,786 A | 10/1993 | Lin et al. | | 585/645 |
| 5,364,826 A | 11/1994 | Kemp | | 502/315 |
| 5,374,748 A | 12/1994 | Rizkalla | | 549/534 |
| 5,380,697 A | 1/1995 | Matusz et al. | | 502/348 |
| 5,380,885 A | 1/1995 | Kemp | | 549/536 |
| 5,387,751 A | 2/1995 | Hayden et al. | | 549/534 |
| 5,407,888 A | 4/1995 | Herzog et al. | | 502/317 |
| 5,418,202 A | 5/1995 | Evans et al. | | 502/348 |
| 5,447,897 A | 9/1995 | Kemp | | 502/303 |
| 5,457,897 A | 10/1995 | Becker | | 34/472 |
| 5,486,628 A | 1/1996 | Kemp | | 549/536 |
| 5,502,020 A | 3/1996 | Iwakura et al. | | 502/317 |
| 5,545,603 A | 8/1996 | Kemp | | 502/347 |
| 5,588,986 A | 12/1996 | Davis et al. | | 95/211 |
| 5,597,773 A | 1/1997 | Evans et al. | | 502/348 |
| 5,626,455 A | 5/1997 | Keller et al. | | 414/288 |
| 5,663,385 A | 9/1997 | Kemp | | 549/536 |
| 5,668,077 A | 9/1997 | Klopries et al. | | 502/347 |
| 5,703,253 A | 12/1997 | Evans et al. | | 549/536 |
| 5,705,661 A | 1/1998 | Iwakura et al. | | 549/534 |
| 5,734,068 A | 3/1998 | Klopries et al. | | 549/536 |
| 5,739,075 A | 4/1998 | Matusz | | 502/302 |
| 5,801,259 A | 9/1998 | Kowaleski | | 549/536 |
| 5,935,894 A | 8/1999 | Kanazirev | | 502/341 |
| 6,103,916 A | 8/2000 | Takada et al. | | 549/534 |
| 6,281,160 B1 | 8/2001 | Basset et al. | | 502/332 |
| 6,325,919 B1 | 12/2001 | Koyama et al. | | 208/134 |
| 6,368,998 B1 | 4/2002 | Lockemeyer | | 502/347 |
| 6,372,925 B1 | 4/2002 | Evans et al. | | 549/536 |
| 6,498,122 B2 | 12/2002 | Nakashiro | | 502/347 |
| 6,511,938 B1 * | 1/2003 | Liu et al. | | 502/347 |
| 6,631,890 B1 | 10/2003 | Lau | | 261/94 |
| 6,656,874 B2 | 12/2003 | Lockemeyer | | 502/347 |
| 6,717,001 B2 | 4/2004 | Evans et al. | | 549/536 |
| 7,259,129 B2 | 8/2007 | Matusz et al. | | 502/347 |
| 2002/0010094 A1 | 1/2002 | Lockemeyer | | 502/439 |
| 2002/0010378 A1 | 1/2002 | Kakimoto et al. | | 568/867 |
| 2002/0137957 A1 | 9/2002 | Lockemeyer | | 549/534 |
| 2004/0224841 A1 | 11/2004 | Matusz et al. | | 502/347 |
| 2004/0225138 A1 | 11/2004 | McAllister et al. | | 549/523 |
| 2004/0260103 A1 | 12/2004 | Matusz et al. | | 549/534 |
| 2006/0065064 A1 | 3/2006 | Richard et al. | | 73/865.5 |
| 2008/0015393 A1 | 1/2008 | Matusz et al. | | 568/497 |

FOREIGN PATENT DOCUMENTS

| | | |
|---|---|---|
| EP | 0211521 | 7/1986 |
| EP | 266015 | 5/1988 |
| EP | 0563414 | 3/1992 |
| EP | 0568978 | 5/1993 |
| EP | 0327356 | 3/1995 |
| EP | 0716884 | 6/1996 |
| EP | 0937498 | 8/1999 |
| EP | 1002575 | 5/2000 |
| EP | 1277698 | 1/2003 |
| EP | 1201301 | 3/2005 |
| FR | 2005978 | 4/1969 |
| GB | 1257352 | 12/1971 |
| GB | 1489335 | 10/1974 |
| JP | 56105750 | 8/1981 |
| JP | 56164013 | 12/1981 |
| RU | 2133642 | 7/1999 |
| WO | WO9623585 | 8/1996 |
| WO | WO9641848 | 12/1996 |
| WO | WO0196324 | 12/2001 |
| WO | WO0226370 | 4/2002 |
| WO | WO03072246 | 9/2003 |
| WO | WO2004094055 | 11/2004 |
| WO | WO2004101144 | 11/2004 |
| WO | WO2005023417 | 3/2005 |

OTHER PUBLICATIONS

Fulton, James W., "Selecting the Catalyst Configuration," *Chemical Engineering*, May 12, 1986, pp. 97-101.

International Search Report of PCT/US2005/033758 dated Apr. 12, 2006.

W.J. Beek and K.M.K. Mattzall, "Transport Phenomena", J. Wiley and Sons Ltd., 1975, p. 114.

Journal of the American Chemical Society 6 (1938) pp. 309-316.

Perry's Chemical Engineer's Handbook, $6^{th}$ Edition, R.H. Perry, et al. p. 18-24, 1983.

Kirk-Othermer Encyclopedia of Chemical Technology, $3^{rd}$ Edition, vol. 9, 1980 pp. 445-447.

* cited by examiner

PROCESS FOR SELECTING SHAPED PARTICLES FOR USE IN A PACKED BED

This application claims the benefit of U.S. Provisional Application No. 60/612,696 filed Sep. 24, 2004 the entire disclosure of which is hereby incorporated by reference.

FIELD OF THE INVENTION

The invention relates to a process for selecting shaped particles for use in a system which comprises a tube which is capable of being packed with shaped particles to form a packed bed in the tube. The invention also relates to a method for installing the system, which method comprises selecting shaped particles and packing the tube with shaped particles as selected to form the packed bed in the tube. The invention also relates to a process for reacting a gaseous feedstock in the system so installed, wherein the shaped particles are catalyst particles suitable for reacting the feedstock. In particular, the catalyst comprises silver on a support, and the process for reacting a gaseous feedstock is a process for the epoxidation of an olefin. The invention also relates to a computer program, a computer program product and a computer system.

BACKGROUND OF THE INVENTION

Ethylene oxide is an important industrial chemical used as a feedstock for making such chemicals as ethylene glycol, ethylene glycol ethers, ethanol amines and detergents. Other industrially important olefin oxides are for example propylene oxide and butadiene oxide. A method for manufacturing an olefin oxide is by the catalyzed partial oxidation of the olefin with oxygen yielding the olefin oxide, which is referred to hereinafter by "olefin epoxidation". The olefin oxide so manufactured may be reacted with water, an alcohol or an amine to produce a 1,2-diol, a 1,2-diol ether or an alkanol amine.

In generally applied methods of olefin epoxidation, a gaseous feedstream containing the olefin and oxygen is passed over a packed bed of shaped catalyst particles positioned in one or more reactor tubes. The catalyst generally comprises silver on a support. The feedstream is compressed in order to overcome the resistance to flow of the packed bed. During normal operation, the catalyst is subject to an aging-related performance decline. The aging manifests itself by a reduction in the activity of the catalyst. Usually, when a reduction in activity of the catalyst is manifest, the reaction temperature is increased in order to compensate for the reduction in activity. The reaction temperature may be increased until it becomes undesirably high, at which point in time the catalyst is deemed to be at the end of its lifetime and would need to be exchanged.

When the catalyst needs to be exchanged, an opportunity arises to reconsider the conditions of economically optimal operation of the olefin epoxidation process. Such optimal conditions may have changed as the economy of operating the process has changed. For example, the economy may have changed as a result of changes in the values of the olefin and/or oxygen used as components of the feedstream, changes in the value of one or more of the olefin oxide, 1,2-diol, 1,2-diol ether, and alkanol amine products, and/or changes in the value of energy used, for example, for compression of the feedstream. Also for the process to be operated in a new plant, consideration has to be given to the conditions of economically optimal operation.

In one aspect, the consideration of the economically optimal operating conditions involves the balance between, on the one hand achieving the potential for a high productivity by packing a large quantity of shaped catalyst particles in the reactor tubes, and, on the other hand achieving a low pressure difference over the packed bed, that is to minimize compression costs. The quantity of shaped catalyst particles packed in a reactor tube may be expressed as the volume fraction of the packed bed occupied by the catalyst particles or by the packing density. It goes without saying that, generally, packing a larger quantity of shaped catalyst particles in the reactor tube and maintaining the flow rates goes hand-in-hand with a higher pressure difference over the catalyst bed, and, hence with higher compression costs.

Given the dimensions of the packed bed in the reactor tubes and the shape of the catalyst particles, the quantity of shaped catalyst particles packed in the packed bed and the pressure difference over the packed bed may be governed by the dimensions of the catalyst particles. Selecting the dimensions of the shaped catalyst particles such that desired values of the quantity and/or the pressure difference can be accomplished requires an extensive trial and error experimental program.

The selection process and the reasons behind the selection process as described hereinbefore in the context of olefin epoxidation are in an analogous manner applicable to many other processes which involves shaped particles packed in a tube, for example absorption processes, for example, using guard beds; heat exchange processes; and conversion processes other than olefin epoxidation, such as processes for manufacturing maleic acid and vinyl acetate, hydrogenation processes, Fisher-Tropsch synthesis, and catalytic conversion of exhaust gases, for example automotive exhaust gas or industrial exhaust gas.

SUMMARY OF THE INVENTION

The present invention provides a process for selecting shaped particles for use in a system which comprises a tube which is capable of being packed with shaped particles to form a packed bed in the tube, wherein the process comprises:
  defining a desired value of one or more properties of the packed bed,
  calculating dimensions of the shaped particles such that a packed bed in the tube of the shaped particles having the calculated dimensions meets or substantially meets the desired value(s), and
  selecting shaped particles in accordance with the calculated dimensions, wherein the said one or more properties of the packed bed comprise one or more of:
  the volume fraction which is occupied by shaped particles,
  the packing density, and
  the resistivity for a gas flowing through the packed bed causing a pressure difference between a gas inlet and a gas outlet of the packed bed, which resistivity is defined by the expression:

$$\Delta P = R \times \rho \times V^2,$$

wherein $\Delta P$ represents the pressure difference per unit length of the packed bed, R represents the resistivity, $\rho$ represents the density of the gas and V represents the superficial gas velocity, wherein the density of the gas and the superficial gas velocity are as measured at the average value of gas inlet temperature and gas outlet temperature of the packed bed and the average value of gas inlet pressure and gas outlet pressure of the packed bed.

The present invention also provides a process for selecting shaped particles ("replacement shaped particles", hereinafter) which are suitable for replacing shaped particles packed in an existing packed bed in a tube, wherein the process comprises:

defining a desired value of a relative change in the pressure difference over the packed bed per unit length of the packed bed when the packed bed is subjected to conditions of a gas flowing through the packed bed, wherein the relative change results from the said replacement of the shaped particles by the replacement shaped particles, calculating dimensions of shaped particles such that a packed bed in the tube of the shaped particles having the calculated dimensions exhibits a relative change in the pressure difference per unit length of the packed bed under the said conditions of gas flow which meets or substantially meets the desired value of the relative change in the pressure difference, and selecting the replacement shaped particles in accordance with the calculated dimensions.

The present invention also provides a method for installing a system comprising a tube which is capable of being packed with shaped particles to form a packed bed in the tube, which method comprises:

selecting shaped particles in accordance with this invention, and packing the tube with shaped particles as selected to form the packed bed in the tube.

If applicable, at least a portion, if not all, of the shaped particles packed in the existing packed bed is removed prior to packing the tube with shaped particles as selected.

The present invention also provides a process for reacting a gaseous feedstock in a system installed in accordance with this invention, wherein the shaped particles are catalyst particles suitable for reacting the feedstock, comprising contacting the feedstock with the shaped particles at reaction conditions. In a typical embodiment, the process is a process for the epoxidation of an olefin, the gaseous feedstock comprises the olefin and oxygen, and the catalyst comprises silver on a support. In such embodiments, the invention further provides a process for the manufacture of a 1,2-diol, a 1,2-diol ether or an alkanol amine, comprising reacting an olefin oxide with water, an alcohol or an amine, wherein the olefin oxide is prepared according to this invention.

The present invention also provides a computer program comprising a computer readable program code for instructing a central processing unit of a computer system to execute one or more calculations comprised in the processes of the present invention.

The present invention also provides a computer program product comprising a memory medium and a computer readable program code recorded on the memory medium, wherein the computer readable program code is suitable for instructing a central processing unit to execute one or more calculations comprised in the processes of the present invention.

The present invention also provides a computer system comprising the computer program product of the present invention and a central processing unit, wherein the central processing unit is configured to receive and execute instructions read from the computer program product.

DETAILED DESCRIPTION OF THE INVENTION

Figure 1:
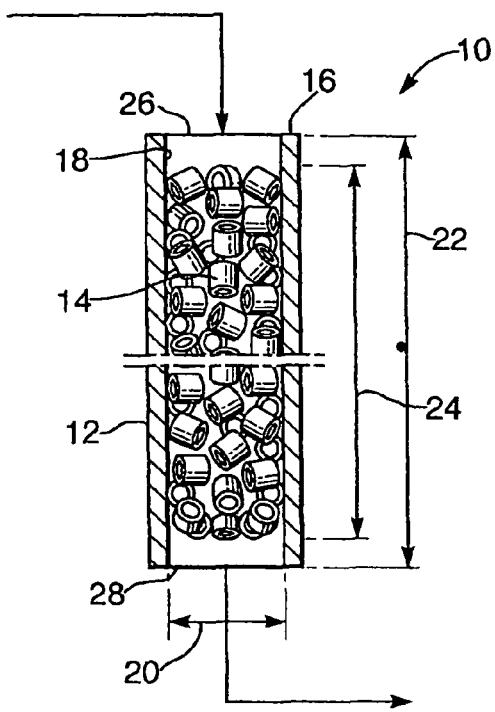
FIG. 1 depicts a tube which comprises a packed bed in accordance with this invention.

The invention enables the selection of shaped particles such that a packed bed of the shaped particles when packed in the tube has or approaches desired properties. The desired properties may be anyone, or a combination of, the volume fraction of the packed bed which is occupied by the shaped particles, the packing density, and the resistivity of the packed bed for a gas flowing through the packed bed causing a pressure difference over the packed bed. An important aspect of the invention is the recognition that the shaped particles may be selected on the basis of calculations using mathematical expressions, such as the mathematical expressions described herein, rather than that the selection is to be based on an extensive series of trial and error experiments.

It has been found that shaped particles may be selected which provide an improved balance of the quantity of shaped particles packed in the packed bed relative to the pressure difference over the packed bed. This may be an improvement relative to the situation in which the packed bed comprises conventional shaped particles, such as for example the standard 8 mm cylinders, which have been employed widely and for many years in, for example, ethylene epoxidation processes. The improved balance may be obtained by changing, in particular increasing, the ratio of the cylinder diameter to the cylinder bore diameter of the cylinder geometric configuration. This is truly unexpected since attempts to improve the performance of these catalysts by modifying the geometry of the cylinder geometric configuration do not seem to have received attention. Further, increasing the ratio of the cylinder diameter to the cylinder bore diameter allows for a greater wall thickness of the cylinder geometric configuration, in particular at equal cylinder diameter, which leads to improved crush strength of the shaped particle.

It is also unexpected that a larger quantity of shaped particles can be packed in the tube to obtain an increase in the packing density either without observing a larger pressure difference or with observing an incremental increase in pressure difference that is less than expected, particularly based on engineering correlations, for example the Ergun Correlation, see W. J. Beek and K. M. K. Muttzall, "Transport Phenomena", J. Wiley and Sons Ltd., 1975, p. 114, which is incorporated herein by reference.

Thus, in accordance with this invention, the geometric combination of inside tube diameter and the geometric dimensions of the shaped particles can provide for an unexpected reduction in pressure difference, when in use and relative to conventional systems, without a significant decrease in the quantity of shaped particles present in the packed bed. In many instances, and preferably, the quantity of shaped particles is greater than that of conventional systems while still providing for a reduction in the pressure difference when in use. A relevant geometric dimension is the ratio of cylinder length to the cylinder diameter. Another relevant geometric dimension is the ratio of the cylinder diameter to cylinder bore diameter. These ratios are described in detail hereinafter.

As used herein, "packing density" represents the mass of the shaped particles per unit volume of the packed bed. As used herein, "particle density" represents the mass of a particle per unit volume of the particle within the boundaries of the particle, that is including the volume of pores which may or may not be present in the particle. The volume of the particle within the perimeters of the particle does not include, for example, the volume of a bore hole or the volume between particles in a packed bed. Hence, the particle density is deemed not to be dependent of the shape and dimensions of the particle. On the other hand, for a given particle material, the particle density is dependent of the volume of pores present in the particle. When pores are absent, the particle density is equal to the material density, which may also be referred to as skeletal density.

Reference is made to FIG. 1, which depicts a system 10, which may in some embodiments be a reactor system, comprising the tube 12 and the packed bed 14 contained within the tube 12. Tube 12 has a tube wall 16 with an inside tube surface 18 and inside tube diameter 20 that define a zone, which may in some embodiments be a reaction zone, wherein is contained packed bed 14, and a zone diameter 20. Tube 12 has a tube length 22 and the packed bed 14 contained within the zone has a bed length 24.

In typical embodiments, the inside cross section of the tube perpendicular to the tube axis ("tube cross section", hereinafter) is circular, which means that the tube, internally, represents an elongated cylinder. In other embodiments, the tube cross section may be, for example, rectangular, squared, hexagonal, or, in particular, oval. As used herein, for tubes of which the tube cross section is non-circular, the inside tube diameter as specified is deemed to represent the equivalent circular diameter, which equivalent circular diameter represents the diameter of a circle which has a circumferential length the same as the circumferential length of the non-circular tube cross section. For tubes of which the tube cross section is non-circular, the ratio of the largest dimension of the tube cross section to the smallest dimension of the tube cross section is typically in the range of from more than 1 to at most 10, more typically from more than 1 to at most 5, in particular from more than 1 to at most 2.

The inside tube diameter 20 may typically be at most 120 mm, more typically at most 80 mm, in particular at most 60 mm. Typically, the inside tube diameter is at least 10 mm, more typically at least 15 mm, in particular at least 20 mm. Typically, the tube is an elongated tube. The tube cross section defines the shape and dimensions of the corresponding cross section of the packed bed. The inside tube diameter equals the outside diameter of the packed bed. Preferably, the length 22 of the tube is at least 3 m, more preferably at least 5 m. Preferably the tube length 22 is at most 25 m, more preferably at most 20 m. Preferably, the wall thickness of the tube is at least 0.5 mm, more preferably at least 1 mm, and in particular at least 2 mm. Preferably, the wall thickness of the tube is at most 10 mm, more preferably at most 5 mm, and in particular at most 4 mm.

In embodiments in which the packed bed is a catalyst bed, the tube 12 may contain, outside the bed length 24, a separate bed of particles of a non-catalytic or inert material for the purpose of, for example, heat exchange with a feedstream and/or another such separate bed for the purpose of, for example, heat exchange with a reaction product.

Preferably, the bed length 24 is at least 3 m, more preferably at least 5 m. Preferably the bed length 24 is at most 25 m, more preferably at most 20 m. The tube 12 further has an gas inlet tube end 26 into which a feedstream may be introduced and a gas outlet tube end 28 from which, for example, a reaction product may be withdrawn.

In some embodiments, the present invention involves defining a desired value of one or more properties of the packed bed. Such properties include one or more of
the volume fraction which is occupied by shaped particles,
the packing density, and
the resistivity for a gas flowing through the packed bed causing a pressure difference between a gas inlet and a gas outlet of the packed bed.

In general, the value of the property will be defined in accordance with economically optimal conditions of operation of the process which comprises operating the packed bed. Preferably, the properties of which a desired value is defined comprise (1) the volume fraction which is occupied by shaped particles or the packing density, and (2) the resistivity.

The desired value of the volume fraction which is occupied by shaped particles may in some embodiments be at least 0.2, more typically at least 0.3, and in particular at least 0.35. The desired value of the volume fraction which is occupied by shaped particles may in some embodiments be at most 1, more typically at most 0.8, in particular at most 0.7.

The desired value of the packing density may in some embodiments be at least 100 kg/m$^3$, more typically at least 300 kg/m$^3$, and in particular at least 500 kg/m$^3$. The desired value of the packing density may in some embodiments be at most 1600 kg/m$^3$, and more typically at most 1400 kg/m$^3$, and in particular at most 1200 kg/m$^3$, for example at most 1000 kg/m$^3$.

As used herein, the resistivity R is defined by the expression:

$$\Delta P = R \times \rho \times V^2,$$

wherein $\Delta P$ represents the pressure difference per unit length of the packed bed, R represents the resistivity, $\rho$ represents the density of the gas and V represents the superficial gas velocity, wherein the density of the gas and the superficial gas velocity are as measured at the average value of gas inlet and gas outlet temperature and the average value of gas inlet and gas outlet pressure of the packed bed. In general terms, the expression defining the resistivity R is known to the skilled person as the Leva Correlation. Reference may be made to "Perry's Chemical Engineer's Handbook", 6$^{th}$ Edition, R. H. Perry et al. (Editors), p. 18-24, 1983, which is incorporated herein by reference.

The desired value of the resistivity R may in some embodiments be at least 0.05 mm$^{-1}$, more typically at least 0.1 mm$^{-1}$, and in particular at least 0.2 mm$^{-1}$. The desired value of the resistivity R may in some embodiments be at most 5 mm$^{-1}$, more typically at most 3 mm$^{-1}$, and in particular at most 2.5 mm$^{-1}$.

Figure 2:
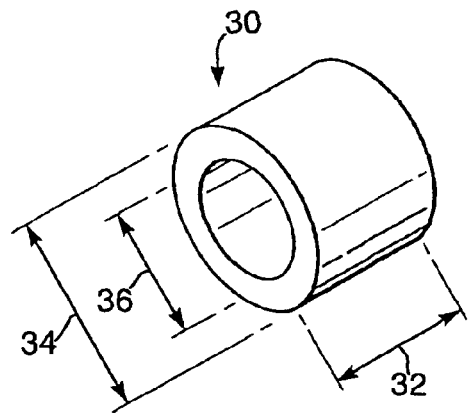
FIG. 2 depicts a shaped particle which may be used in this invention and which has a cylinder geometric configuration.

The shape of the shaped particles may be chosen from a wide range of available shapes, for example, cylinders, saddles, spheres, and doughnuts. The shaped particles have preferably a cylinder geometric configuration, which may or may not be hollow. With reference to FIG. 2, the shaped particles having a cylinder geometric configuration 30 may have a cylinder length 32, typically from 4 to 20 mm, more typically from 5 to 15 mm; a cylinder diameter 34, typically from 4 to 20 mm, more typically from 5 to 15 mm; and a cylinder bore diameter 36, typically from 0.1 to 6 mm, preferably from 0.2 to 4 mm. The ratio of the cylinder length 32 to the cylinder diameter 34 is typically in the range of from 0.5 to 2, more typically from 0.8 to 1.5, in particular from 0.9 to 1.2. In the absence of a bore, that is when the cylinder geometry is not hollow, the cylinder bore diameter is deemed to be zero. The ratio of the cylinder diameter 34 to the cylinder bore diameter 36 may typically be in the range of from 2.5 to 1000, more typically from 2.8 to 500, in particular from 3 to 200.

When the inside tube diameter is less than 28 mm, the ratio of the inside tube diameter 20 to the cylinder diameter 34 may typically be in the range of from 1.5 to 7, more typically from 2 to 6, in particular from 2.5 to 5. When the inside tube diameter is at least 28 mm, the ratio of the inside tube diameter 20 to the cylinder diameter 34 may typically be in the range of from 2 to 10, more typically from 2.5 to 7.5, in particular from 3 to 5.

Figure 4A:
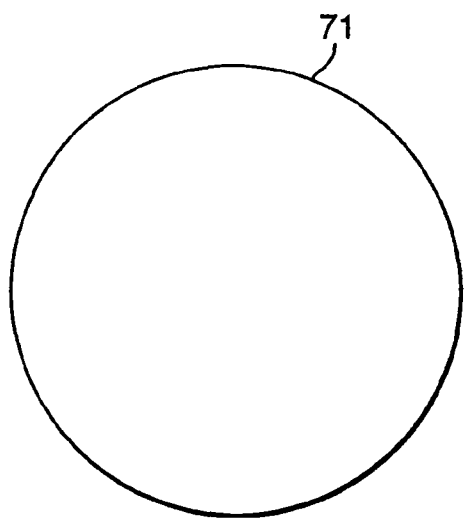
FIG. 4 depicts drawings of the cross-sections of the outside perimeters of (a) the shaped support material being an ideal cylinder, and (b) a cross-section of the shaped support material being a deviation from an ideal cylinder.
Figure 4B:
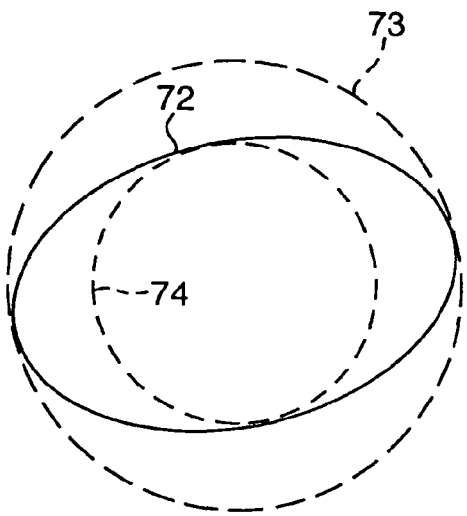

The skilled person will appreciate that in relation to the shaped particles for use in a packed bed the expression "cylinder" does not necessarily mean that the cylinder geometric configuration comprises an exact cylinder. The expression "cylinder" is meant to include insignificant deviations from an exact cylinder. For example, the cross-section of the outer perimeter of the cylinder geometric configuration perpendicular to the cylinder axis is not necessarily an exact circle 71, as depicted in FIG. 4. Also, the axis of the cylinder geometric configuration may be approximately straight and/or the cylinder diameter of the cylinder geometric configuration may be approximately constant along the axis. Insignificant deviations include, for example, cases where the outside perimeter of the cylinder can be positioned in an imaginary tube-shaped space defined by two imaginary exact coaxial cylinders of virtually the same diameters, whereby the diameter of the imaginary inner cylinder is at least 70%, more typically at least 80%, in particular at least 90%, of the diameter of the imaginary outer cylinder, and the imaginary cylinders are chosen such that the ratio of their diameters is the closest possible to 1. In such cases the diameter of the imaginary outer cylinder is deemed to be the cylinder diameter 34 of the cylinder geometric configuration. FIG. 4 depicts in a cross-sectional view, taken perpendicular to the axis of the imaginary cylinders 73 and 74, the outside perimeter 72 of the cylinder geometric configuration, the imaginary outer cylinder 73 and the imaginary inner cylinder 74.

Similarly, the skilled person will appreciate that the bore, if any, of the cylinder geometric configuration may not be necessarily exactly cylindrical, the axis of the bore may be approximately straight, the cylinder bore diameter may be approximately constant, and/or the axis of the bore may be displaced, or may angle, relative to the axis of the cylinder. If the cylinder bore diameter changes over the length of the bore, the cylinder bore diameter is deemed to be the largest diameter at a bore end. If the bore is not exactly circular in cross-section, the widest dimension is deemed to be the cylinder bore diameter. Also, the void space provided by a bore may be divided over two or more bores, for example 2, 3, or even 4, or 5 bores, in which case the diameters of the bores are such that the total of the cross-sectional areas of the bores is equal to the cross-sectional area of a single bore having a cylinder bore diameter, as specified herein.

In preferred embodiments, the cylinder geometric configuration is intended to be a cylinder having a bore along the axis of the cylinder.

It is understood that the dimensions of the cylinder geometric configuration are approximate, since, methods of manufacturing the shaped particles are not necessarily precise. Thus, there may be variations in the dimensions of the individual shaped particles which may be used in the practice of this invention. If that is the case, a relevant dimension of the shaped particles, as defined herein, is deemed to represent the number average of the dimension in question as measured for 100 randomly chosen individual particles. The variations may be such that typically at least 90%, more typically at least 95%, in particular 100% of the randomly chosen individual particles have the dimension in question within from 80 to 120% of the number average of the dimension. More in particular, the variations may be such that at least 90%, more typically at least 95%, in particular 100% of the randomly chosen individual particles have the dimension in question within from 90 to 110% of the number average of the dimension.

In some embodiments, the invention involves a process for selecting replacement shaped particles which are suitable for replacing shaped particles packed in an existing packed bed in a tube. Typically, the shaped particles packed in the existing packed bed have the cylinder geometric configuration, as defined hereinbefore, and in particular they are "standard 8 mm cylinders". As used herein, shaped particles in the form of "standard 8 mm cylinders" have a cylinder length in the range of from 8 to 9 mm, a cylinder diameter in the range of from 8 to 9 mm and a cylinder bore diameter in the range of from 2.5 to 3.5 mm. The replacement shaped particles have typically also the cylinder geometric configuration, as defined hereinbefore. In particular, the replacement shaped particles have the cylinder geometric configuration when the shaped particles packed in the existing packed bed are "standard 8 mm cylinders". In the selection process of these embodiments a desired value is defined for a relative change in the pressure difference per unit length of the packed bed when the bed is subjected to conditions of a gas flowing through the packed bed. The relative change in the pressure difference results from replacing the shaped particles of the existing bed by the selected shaped particles.

The desired value of the relative change in the pressure difference, that is $(\Delta P' - \Delta P_1)/\Delta P_1$ as further defined hereinafter, may in some embodiments be at least −0.8, more typically at least −0.7, and in particular at least −0.6. The desired value of the relative change in the pressure difference may in some embodiments be at most 5, more typically at most 4, preferably at most 3, more preferably at most 1, in particular at most 0.5, more in particular at most 0.2. A negative value of the relative change in the pressure difference points to a decrease in the pressure difference, whereas a positive value points to an increase of the pressure difference, relative to the pressure difference exhibited by the existing packed bed. The value of the change is relative to the situation of the existing packed bed.

The dimensions of the shaped particles may be calculated by using relationships based on the expressions as described herein. The calculation may be an iterative calculation. The calculation may also be performed in an analytical manner by resolving relationships in the form of equations based on the expressions. Graphical methods as a means of calculating may be used as well. The calculation may yield one or more sets of dimensions, for example two or three sets of dimensions, for shaped particles such that a packed bed of the shaped particles formed in the tube meets or substantially meets the desired values. The skilled person will understand that in some embodiments one or more of the dimensions of the shaped particles may be freely chosen as input parameters of the calculation, and that other dimensions will then follow as a result of the calculation. It is an advantage of the invention that the said packed bed of the shaped particles having calculated dimensions, which is meeting or substantially meeting the desired value(s), may be a notional packed bed, because by using the invention there is no further need to physically provide a packed bed for the purpose of testing the properties for which desired values have been defined. As used herein, by "substantially meets" is meant that the packed bed meets the property in question typically within the range of from 70 to 130% of the desired value, more typically within the range of from 80 to 120% of the desired value, in particular within the range of from 90 to 110% of the desired value, and more in particular within the range of from 95 to 105% of the desired value. The calculated dimensions, together with any freely chosen dimensions, if applicable, may then be compared with the dimensions of available shaped particles, for example commercially available shaped particles or shaped particles which may be manufactured using available commercial equipment, such as a die plate for an extruder having suitable dimensions. A suitable selection may be made from the available shaped particles. As an alternative, shaped particles of the calculated dimensions may be made on purpose. In such a way, shaped particles may be selected in accordance with the calculated dimensions. Suitably, the dimensions of the selected shaped particles may then be used in the relationships, in order to verify whether the packed bed of the selected shaped particles to be formed in the tube will meet or substantially meet the desired values.

As an example, the dimensions of the shaped particles having the cylinder geometric configuration may be calculated. The dimensions may be calculated by using one or more relationships which can be defined by mathematical expressions which depend on the property of the packed bed for which a desired value has been defined.

When a desired value has been defined for the volume fraction of the packed bed which is occupied by shaped particles, the mathematical expression may be:

$$V_p = a + b \times (L/D_o) + c \times D_i + d \times D_o^2 + e \times D_t, \text{ or}$$

$$V_p = a' \times [(D_t/D_o)^2/(b' + (D_t/D_o)^2)] - c' \times [(D_t/D_o)^2]$$

wherein:

$V_p$ represents the desired value of the volume fraction of the packed bed which is occupied by shaped particles, L represents the cylinder length, $D_o$ represents the cylinder diameter, $D_i$ represents the cylinder bore diameter, $D_t$ represents the inside diameter of the tube, and each of a, a', b, b', c, c', d and e represents a constant having a dimension accommodating the dimension of the corresponding term of the expression.

When a desired value has been defined for the packing density, the mathematical expression may be:

$$PD = D_e \times [a + b \times (L/D_o) + c \times D_i + d \times D_o^2 + e \times D_t], \text{ or}$$

$$PD = D_e \times [a' \times [(D_t/D_o)^2/(b' + (D_t/D_o)^2)] - c' \times [(D_t/D_o)^2]],$$

wherein

PD represents the desired value of the packing density,

L, $D_o$, $D_i$ and $D_t$ are as defined hereinbefore, $D_e$ represents the particle density, and each of a, a', b, b', c, c', d, and represents a constant having a dimension accommodating the dimension of the corresponding term of the expression.

When a desired value has been defined for the resistivity, the mathematical expression may be:

$$R = l + m \times (L/D_o) + n \times D_o + p \times D_i + q \times L + r \times D_t,$$

wherein:

R represents the desired value of the resistivity,

L, $D_o$, $D_i$ and $D_t$ are as defined hereinbefore, and each of l, m, n, p, q and r represents a constant having a dimension accommodating the dimension of the corresponding term of the expression.

When a desired value has been defined for the relative change in the pressure difference, the mathematical expression may be:

$$(\Delta P' - \Delta P_1)/\Delta P_1 = s + t \times (L/D_o) + u \times D_o + v \times D_i + w \times L + y \times D_t,$$

wherein:

$\Delta P'$ represents the pressure difference per unit length of the packed bed, $\Delta P_1$ represents the pressure difference per unit length of the existing packed bed, that is the packed bed of standard 8 mm cylinders, $(\Delta P' - \Delta P_1)/\Delta P_1$ represents the desired value of the relative change in the pressure difference, L, $D_o$, $D_i$, and $D_t$ are as defined hereinbefore, and each of s, t, u, v, w, and y represents a constant having a dimension accommodating the dimension of the corresponding term of the expression.

The variables present in the mathematical expressions have certain dimensions and may be expressed in units in accordance with their dimensions. In typical embodiments, the units may be defined as follows:

$V_p$ is expressed as a fraction of 1,

PD is expressed in kg/m$^3$,

R is expressed in mm$^{-1}$, $(\Delta P' - \Delta P_1)/\Delta P_1$ is a dimensionless number, which is above $-1$, L is expressed in mm, $D_o$ is expressed in mm, $D_i$ is expressed in mm, $D_e$ is expressed in kg/m$^3$, $D_t$ is expressed in mm, and the values of the constants a, a', b, b', c, c', d, e, l, m, n, p, q, r, s, t, u, v, w and y may be in the ranges as indicated by "typical", "preferred" and "more preferred" in Table I.

With the variables having the units as defined as specified hereinbefore, the constants a, a', b, b', c, c', d, e, l, m, n, p, q, r, s, t, u, v, w and y may have, as an example, the set of values provided as indicated in Table I under "Example I", or as indicated in Table I under "Example II".

TABLE I

|  | typical | preferred | more preferred | Example I | Example II |
|---|---|---|---|---|---|
| a | from 0.2 to 0.7 | from 0.35 to 0.55 | from 0.42 to 0.5 | 0.46 | 0.458969 |
| a' | from 0.3 to 1.0 | from 0.5 to 0.8 | from 0.62 to 0.68 | 0.65 | 0.64834 |
| b | from −0.2 to 0.1 | from −0.1 to 0.05 | from −0.053 to 0.016 | −0.018 | −0.018359 |
| b' | From −1 to 6 | from 1 to 4 | from 1.7 to 3 | 2.35 | 2.3473 |

TABLE I-continued

| | typical | preferred | more preferred | Example I | Example II |
|---|---|---|---|---|---|
| c | from −0.05 to 0.01 | from −0.03 to −0.01 | from −0.025 to −0.017 | −0.021 | −0.020796 |
| c' | From 0.1 to 1.5 | from 0.5 to 0.85 | from 0.59 to 0.77 | 0.68 | 0.68335 |
| d | from −0.001 to 0.0002 | from −0.0007 to −0.0001 | from −0.00055 to −0.00022 | −0.00038 | −0.000384 |
| e | from 0.001 to 0.007 | from 0.0025 to 0.0055 | from 0.0032 to 0.0045 | 0.0038 | 0.003835 |
| l | from −1 to 7 | From 1.5 to 5 | from 2.6 to 4.3 | 3.5 | 3.4787 |
| m | from −5 to 2 | from −3.5 to 0 | from −2.7 to −0.9 | −1.8 | −1.8359 |
| n | from −0.8 to 0 | from −0.6 to −0.15 | from −0.47 to −0.25 | −0.36 | −0.3605 |
| p | from −0.2 to 0.05 | from −0.12 to −0.02 | from −0.094 to −0.046 | −0.07 | −0.0702 |
| q | from −0.3 to 0.6 | from −0.1 to 0.4 | from 0.01 to 0.25 | 0.13 | 0.1337 |
| r | from 0.01 to 0.07 | from 0.03 to 0.05 | from 0.035 to 0.042 | 0.038 | 0.0384 |
| s | from −5 to 20 | From 3 to 15 | from 6 to 12 | 8.7 | 8.72936006 |
| t | from −20 to 5 | From −12 to 0 | from −8.8 to −3.1 | −5.9 | −5.92688308 |
| u | from −2.5 to 0.5 | from −1.5 to 0 | from −1.1 to −0.4 | −0.78 | −0.784224 |
| v | from −0.4 to 0.2 | from −0.25 to 0.05 | from −0.18 to −0.03 | −0.11 | −0.10769649 |
| w | from −1 to 2 | from −0.2 to 1.3 | from 0.19 to 0.91 | 0.55 | 0.55308813 |
| y | from −0.06 to 0.03 | from −0.035 to 0.01 | from −0.023 to −0.002 | −0.013 | −0.01270296 |

By way of an example, for alumina particles having a particle density of 1550 kg/m$^3$, the following relationship was found for the packing density:

$$PD=721.545-28.8624\times(L/D_o)-32.6931\times D_i-0.6033\times D_o^2+6.0295\times D_t,$$

in which PD, L, $D_o$, $D_i$ and $D_t$ have the units as defined hereinbefore.

The present invention also provides a method for installing a system. The system comprises a tube which is capable of being packed with shaped particles to form a packed bed in the tube. Examples of suitable systems are systems for use in an absorption process, for example guard beds for capturing moisture or sulfur compounds; systems for heat exchange, for example a packed bed of inert material for the purpose of heat exchange in combination with a packed catalyst bed, as described hereinbefore; and systems which are reactor systems comprising a packed bed of catalyst particles. Such reactor systems may be used in, for example, a process for manufacturing an olefin oxide by the epoxidation of an olefin, maleic acid by partial catalytic oxidation of benzene or vinyl acetate by partial catalytic oxidation of ethylene in the presence of acetic acid, in a hydrogenation process, in a process for Fisher-Tropsch synthesis, or in a catalytic conversion process for exhaust gasses, for example, industrial or automotive exhaust gasses.

The method for installing the system, in accordance with this invention, comprises
  selecting shaped particles in accordance with this invention, and
  packing the tube with shaped particles as selected to form the packed bed in the tube.

The skilled person will appreciate that the properties of the packed bed will to some extent depend on the filling rate, that is the rate at which the shaped particles are poured into the tube. Preferably, the filling rate is so low that the properties of the packed bed are not significantly dependent on the filling rate. Typically the filling rate, expressed as the tube length filled per time unit, is at most 0.5 m/s, more typically the filling rate is at most 0.2 m/s, in particular at most 0.1 m/s, more in particular at most 0.05 m/s. Frequently, in the normal practice of this invention, the filling rate is at least 0.001 m/s, more frequently the filling rate is at least 0.005 m/s. The packed beds specified herein are deemed to be packed beds which have been formed by filing the tube in question at a rate which is so low that the properties of the packed bed are not significantly dependent on the filling rate, by which it is meant that by lowering the filling rate to an infinitely low filling rate the bulk density decreases typically by at most 5%, more typically at most 2%. This may be verified by routine testing, wherein the trend of bulk densities versus filling rate may be extrapolated to a filling rate zero in order to find the bulk density at an infinitely low filling rate.

The present invention also provides a process for reacting a gaseous feedstock in a system installed in accordance with the invention, wherein the shaped particles are catalyst particles suitable for reacting the feedstock. The process for reacting the gaseous feedstock comprises contacting the feedstock with the shaped particles at reaction conditions. Examples of such processes have been given hereinbefore and the skilled person will be able to select a suitable type catalyst for the process in question.

In particular embodiments the process is a process for the epoxidation of an olefin, the gaseous feedstock comprises the olefin and oxygen, and the catalyst comprises silver on a support. By way of an example, a detailed description is given hereinafter of embodiments of this invention which involve a process for the epoxidation of an olefin.

The catalyst typically used for the epoxidation of an olefin is a catalyst comprising silver on a support.

The support may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the support comprises at least 85% w, more typically at least 90% w, in particular at least 95% w α-alumina, frequently up to 99.9% w α-alumina, relative to the weight of the support. Other components of the α-alumina support may comprise, for example, silica, titania, zirconia, alkali metal components, for example sodium and/or potassium components, and/or alkaline earth metal components, for example calcium and/or magnesium components.

The surface area of the support may suitably be at least 0.1 m$^2$/g, preferably at least 0.3 m$^2$/g, more preferably at least 0.5 m$^2$/g, and in particular at least 0.6 m$^2$/g, relative to the mass of the support; and the surface area may suitably be at most 10 m$^2$/g, preferably at most 5 m$^2$/g, and in particular at most 3 m$^2$/g, relative to the mass of the support. "Surface area" as used herein is understood to relate to the surface area as determined by the B.E.T. (Brunauer, Emmett and Teller) method as described in Journal of the American Chemical Society 60 (1938) pp. 309-316. High surface area supports, in particular when they are α-alumina supports optionally comprising in addition silica, alkali metal and/or alkaline earth metal components, provide improved performance and stability of operation.

The water absorption of the support is typically in the range of from 0.2 to 0.8 g/g, preferably in the range of from 0.3 to 0.7 g/g. A higher water absorption may be in favour in view of a more efficient deposition of silver and further elements, if any, on the support by impregnation. However, at a higher water absorption, the support, or the catalyst made therefrom, may have lower crush strength. As used herein, water absorption is deemed to have been measured in accordance with ASTM C20, and water absorption is expressed as the mass of the water that can be absorbed into the pores of the support, relative to the mass of the support.

The preparation of the catalyst comprising silver is known in the art and the known methods are applicable to the preparation of the shaped catalyst particles which may be used in the practice of this invention. Methods of depositing silver on the support include impregnating the support with a silver compound containing cationic silver and performing a reduction to form metallic silver particles. Reference may be made, for example, to U.S. Pat. No. 5,380,697, U.S. Pat. No. 5,739,075, EP-A-266015, and U.S. Pat. No. 6,368,998, which patents are incorporated herein by reference.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity may be obtained by employing a silver content of the catalyst of at least 10 g/kg, relative to the mass of the catalyst. Preferably, the catalyst comprises silver in a quantity of from 50 to 500 g/kg, more preferably from 100 to 400 g/kg.

The catalyst for use in this invention may comprise a promoter component which comprises an element selected from rhenium, tungsten, molybdenum, chromium, and mixtures thereof. Preferably the promoter component comprises, as an element, rhenium.

The promoter component may typically be present in a quantity of at least 0.01 mmole/kg, more typically at least 0.1 mmole/kg, and preferably at least 0.5 mmole/kg, calculated as the total quantity of the element (that is rhenium, tungsten, molybdenum and/or chromium) relative to the mass of the catalyst. The promoter component may be present in a quantity of at most 50 mmole/kg, preferably at most 10 mmole/kg, more preferably at most 5 mmole/kg, calculated as the total quantity of the element relative to the mass of the catalyst. The form in which the promoter component may be deposited onto the support is not material to the invention. For example, the promoter component may suitably be provided as an oxide or as an oxyanion, for example, as a rhenate, perrhenate, or tungstate, in salt or acid form.

When the catalyst comprises a rhenium containing copromoter, rhenium may typically be present in a quantity of at least 0.1 mmole/kg, more typically at least 0.5 mmole/kg, and preferably at least 1.0 mmole/kg, in particular at least 1.5 mmole/kg, calculated as the quantity of the element relative to the mass of the catalyst. Rhenium is typically present in a quantity of at most 5.0 mmole/kg, preferably at most 3.0 mmole/kg, more preferably at most 2.0 mmole/kg, in particular at most 1.5 mmole/kg.

Further, when the catalyst comprises a rhenium containing copromoter, the catalyst may preferably comprise a rhenium copromoter, as a further component deposited on the support. Suitably, the rhenium copromoter may be selected from components comprising an element selected from tungsten, chromium, molybdenum, sulfur, phosphorus, boron, and mixtures thereof. Preferably, the rhenium copromoter is selected from components comprising tungsten, chromium, molybdenum, sulfur, and mixtures thereof. It is particularly preferred that the rhenium copromoter comprises, as an element, tungsten.

The rhenium copromoter may typically be present in a total quantity of at least 0.01 mmole/kg, more typically at least 0.1 mmole/kg, and preferably at least 0.5 mmole/kg, calculated as the element (i.e. the total of tungsten, chromium, molybdenum, sulfur, phosphorus and/or boron), relative to the mass of the catalyst. The rhenium copromoter may be present in a total quantity of at most 40 mmole/kg, preferably at most 10 mmole/kg, more preferably at most 5 mmole/kg, on the same basis. The form in which the rhenium copromoter may be deposited on the support is not material to the invention. For example, it may suitably be provided as an oxide or as an oxyanion, for example, as a sulfate, borate or molybdate, in salt or acid form.

The catalyst preferably comprises silver, the promoter component, and a component comprising a further element, deposited on the support. Eligible further elements may be selected from the group comprising nitrogen, fluorine, alkali metals, alkaline earth metals, titanium, hafnium, zirconium, vanadium, thallium, thorium, tantalum, niobium, gallium and germanium and mixtures thereof. Preferably the alkali metals are selected from lithium, potassium, rubidium and cesium. Most preferably the alkali metal is lithium, potassium and/or cesium. Preferably the alkaline earth metals are selected from calcium and barium. Typically, the further element is present in the catalyst in a total quantity of from 0.01 to 500 mmole/kg, more typically from 0.05 to 100 mmole/kg, calculated as the element on the mass of the catalyst. The further elements may be provided in any form. For example, salts of an alkali metal or an alkaline earth metal are suitable.

As used herein, the quantity of alkali metal present in the catalyst is deemed to be the quantity in so far as it can be extracted from the catalyst with de-ionized water at 100° C. The extraction method involves extracting a 10-gram sample of the catalyst three times by heating it in 20 ml portions of de-ionized water for 5 minutes at 100° C. and determining in the combined extracts the relevant metals by using a known method, for example atomic absorption spectroscopy.

As used herein, the quantity of alkaline earth metal present in the catalyst is deemed to the quantity in so far as it can be extracted from the catalyst with 10% w nitric acid in de-ionized water at 100° C. The extraction method involves extracting a 10-gram sample of the catalyst by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

The olefin for use in the present epoxidation process may be any olefin, such as an aromatic olefin, for example styrene, or a di-olefin, whether conjugated or not, for example 1,9-decadiene or 1,3-butadiene. Mixtures of olefins may be used. Typically, the olefin is a monoolefin, for example 2-butene or isobutene. Preferably, the olefin is a mono-α-olefin, for example 1-butene or propylene. The most preferred olefin is ethylene.

Figure 3:
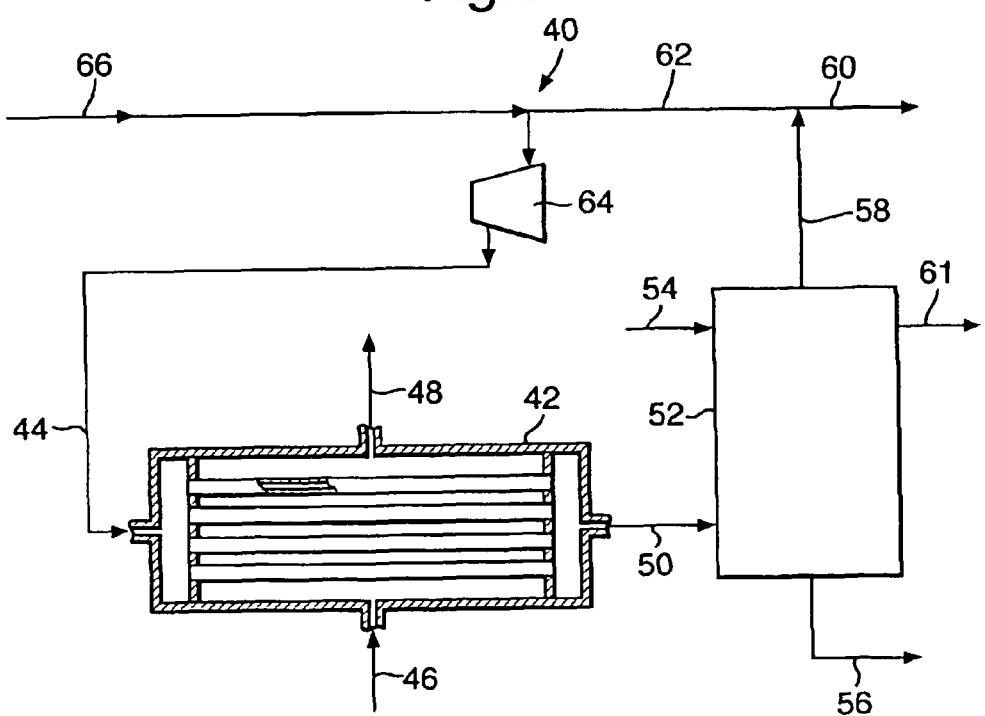
FIG. 3 is a schematic representation of an ethylene oxide manufacturing process which includes certain novel aspects of the invention.

As an illustration of an olefin oxide manufacturing system of this invention, FIG. 3 provides a schematic representation showing a typical ethylene oxide manufacturing system 40 with a shell-and-tube heat exchanger 42 which is equipped with one or more reactor systems as depicted in FIG. 1. Typically a plurality of reactor systems is grouped together into a tube bundle for insertion into the shell of a shell-and-tube heat exchanger. The skilled person will understand that the catalyst particles are packed into the individual tubes such that the tubes and their contents provide the same resistivity when a gas flow passes through the elongated tubes. The number of tubes present in the shell-and-tube heat exchanger 42 is typically in the range of from 1,000 to 20,000, more typically in the range of from 2,000 to 15,000. Ethylene oxide manufacturing system 40 may comprise one or more shell-and-tube heat exchangers 42, for example two, three or four.

A feedstream comprising ethylene and oxygen may be charged via conduit 44 to the tube side of shell-and-tube heat exchanger 42 wherein it is contacted with the packed catalyst bed contained therein. The shell-and-tube heat exchanger 42 is typically operated in a manner which allows an upward or downward flow of gas through the packed catalyst bed. The heat of reaction may be removed and control of the reaction temperature, that is the temperature within the packed catalyst bed, may be achieved by use of a heat transfer fluid, for example oil, kerosene or water, which is charged to the shell side of shell-and-tube heat exchanger 42 by way of conduit 46 and the heat transfer fluid is removed from the shell of shell-and-tube heat exchanger 42 through conduit 48.

The reaction product comprising ethylene oxide, unreacted ethylene, unreacted oxygen and, optionally, other reaction products such as carbon dioxide and water, is withdrawn from the reactor system tubes of shell-and-tube heat exchanger 42 through conduit 50 and passes to separation system 52. Separation system 52 provides for the separation of ethylene oxide from ethylene and, if present, carbon dioxide and water. An extraction fluid such as water may be used to separate these components and is introduced to separation system 52 by way of conduit 54. The enriched extraction fluid containing ethylene oxide passes from separation system 52 through conduit 56 while unreacted ethylene and carbon dioxide, if present, passes from separation system 52 through conduit 58. Separated carbon dioxide passes from separation system 52 through conduit 61. A portion of the gas stream passing through conduit 58 may be removed as a purge stream through conduit 60. The remaining gas stream passes through conduit 62 to recycle compressor 64. A stream containing ethylene and oxygen passes through conduit 66 and is combined with the recycle ethylene that is passed through conduit 62 and the combined stream is passed to recycle compressor 64. Recycle compressor 64 discharges into conduit 44 whereby the discharge stream is charged to the gas inlet of the tube side of the shell-and-tube heat exchanger 42. Ethylene oxide produced may be recovered from the enriched extraction fluid, for example by distillation or extraction.

The olefin concentration in the feedstream may be selected within a wide range. Typically, the olefin concentration in the feedstream will be at most 80 mole-%, relative to the total feed. Preferably, it will be in the range of from 0.5 to 70 mole-%, in particular from 1 to 60 mole-%, on the same basis. As used herein, the feedstream is considered to be the composition which is contacted with the catalyst particles.

The present epoxidation process may be air-based or oxygen-based, see "Kirk-Othmer Encyclopedia of Chemical Technology", 3$^{rd}$ edition, Volume 9, 1980, pp. 445-447. In the air-based process air or air enriched with oxygen is employed as the source of the oxidizing agent while in the oxygen-based processes high-purity (at least 95 mole-%) oxygen is employed as the source of the oxidizing agent. Presently most epoxidation plants are oxygen-based and this is a preferred embodiment of the present invention.

The oxygen concentration in the feedstream passing through conduit 44 may be selected within a wide range. However, in practice, oxygen is generally applied at a concentration which avoids the flammable regime. Typically, the concentration of oxygen applied will be within the range of from 1 to 15 mole-%, more typically from 2 to 12 mole-% of the total feed. The actual safe operating ranges depend, along with the feedstream composition, also on the reaction conditions such as the reaction temperature and the pressure.

An organic halide may be present in the feedstream passing through conduit 44 as a reaction modifier for increasing the selectivity, suppressing the undesirable oxidation of the olefin or the olefin oxide to carbon dioxide and water, relative to the desired formation of the olefin oxide. Organic halides are in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred are ethyl chloride and ethylene dichloride.

The organic halides are generally effective as reaction modifier when used in low concentration in the feed, for example up to 0.01 mole-%, relative to the total feed. It is preferred that the organic halide is present in the feedstream at a concentration of at most $50 \times 10^{-4}$ mole-%, in particular at most $20 \times 10^{-4}$ mole-%, more in particular at most $15 \times 10^{-4}$ mole-%, relative to the total feed, and preferably at least $0.2 \times 10^{-4}$ mole-%, in particular at least $0.5 \times 10^{-4}$ mole-%, more in particular at least $1 \times 10^{-4}$ mole-%, relative to the total feed.

In addition to the olefin, oxygen and the organic halide, the feedstream may contain one or more optional components, for example carbon dioxide, inert gases and saturated hydrocarbons. Carbon dioxide generally has an adverse effect on the catalyst activity. Advantageously, separation system 52 is operated in such a way that the quantity of carbon dioxide in the feedstream through conduit 44 is low, for example, below 2 mole-%, preferably below 1 mole-%, or in the range of from 0.2 to 1 mole-%. Inert gases, for example nitrogen or argon, may be present in the feedstream passing through conduit 44 in a concentration of from 30 to 90 mole-%, typically from 40 to 80 mole-%. Otherwise, the inert gasses may be present in a concentration of from 1 to 10 mole-%. Suitable saturated hydrocarbons are methane and ethane. If saturated hydrocarbons are present, they may be present in a quantity of up to 80 mole-%, relative to the total feed, in particular up to 75 mole-%. Frequently they are present in a quantity of at least 30 mole-%, more frequently at least 40 mole-%. Saturated hydrocarbons may be employed in order to increase the oxygen flammability limit.

The epoxidation process may be carried out using reaction temperatures selected from a wide range. Preferably the reaction temperature is in the range of from 150 to 340° C., more preferably in the range of from 180 to 325° C. Typically, the shell-side heat transfer liquid has a temperature which is 5 to 10° C. lower than the reaction temperature.

In order to reduce the effects of deactivation of the catalyst, the reaction temperature may be increased gradually or in a plurality of steps, for example in steps of from 0.1 to 20° C., in particular 0.2 to 10° C., more in particular 0.5 to 5° C. The total increase in the reaction temperature may be in the range of from 10 to 140° C., more typically from 20 to 100° C. The reaction temperature may be increased typically from a level in the range of from 150 to 300° C., more typically from 200 to 280° C., when a fresh catalyst is used, to a level in the range of from 230 to 340° C., more typically from 240 to 325° C., when the catalyst has decreased in activity due to ageing.

The epoxidation process is preferably carried out at a pressure in the gas inlet tube end 26 in the range of from 1000 to 3500 kPa. "GHSV" or Gas Hourly Space Velocity is the unit volume of gas at normal temperature and pressure (0° C., 1 atm, i.e. 101.3 kPa) passing over one unit of the total volume of packed catalyst bed per hour. Preferably, the GHSV is in the range of from 1500 to 10000 Nm$^3$/(m$^3$·h). Preferably, the process is carried out at a work rate in the range of from 0.5 to 10 kmole olefin oxide produced per m$^3$ of the total packed catalyst bed per hour, in particular 0.7 to 8 kmole olefin oxide produced per m$^3$ of the total packed catalyst bed per hour, for example 5 kmole olefin oxide produced per m$^3$ of the total packed catalyst bed per hour.

The olefin oxide produced in the epoxidation process may be converted into a 1,2-diol, a 1,2-diol ether or an alkanol amine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. If the proportion of water is lowered the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The conversion into the alkanol amine may comprise reacting the olefin oxide with an amine, such as ammonia, an alkyl amine or a dialkyl amine. Anhydrous or aqueous ammonia may be used. Anhydrous ammonia is typically used to favor the production of mono ethanol amine. For methods applicable in the conversion of the olefin oxide into the ethanol amine, reference may be made to, for example U.S. Pat. No. 4,845,296, which is incorporated herein by reference.

The 1,2-diols and 1,2-diol ethers may be used in a large variety of industrial applications, for example in the fields of food, beverages, tobacco, cosmetics, thermoplastic polymers, curable resin systems, detergents, heat transfer systems, etc. Alkanol amines may be used, for example, in the treating ("sweetening") of natural gas.

Unless specified otherwise, the organic compounds mentioned herein, for example the olefins, 1,2-diol ethers, alkanol amines and organic halides, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

In the processes of the present invention, the dimensions of the shaped particles may be calculated by using a computer system. The computer system comprises a computer program product and a central processing unit configured to receive and execute instructions read from the computer program product. The computer program product comprises a memory medium and computer readable program code recorded on the memory medium. The computer readable code is executable by the central processing unit and comprises one or more mathematical expressions for one or more properties of the packed bed, as defined hereinbefore.

A software system may work in conjunction with the computer readable program code to instruct the central processing unit to execute one or more calculations comprised in the processes of the present invention. The software system may be stored on a memory medium which is adapted to interact with the central processing unit. Examples of suitable software systems include EXCEL™, MATLAB™, STATISTICA™, and SAS™. Also included in the present invention is a computer program comprising the computer readable program code for instructing the central processing unit to execute one or more calculations comprised in the processes of the present invention.

The term "memory medium" may include an installation medium, for example, compact disks or floppy disks, a computer system memory, or a nonvolatile memory. Examples of computer system memory include, but are not limited to, DRAM and SDAM. Examples of a nonvolatile memory include, but are not limited to, a magnetic media, for example a hard drive, or optical storage. The memory medium may include other types of memory as well, or combinations thereof.

In an embodiment, the desired values for one or more properties of the packed bed are input via a keyboard into the central processing unit. The software system may be stored on a separate memory medium than the computer program product. The central processing unit is configured to receive and execute instructions from both the software system and the computer readable program code.

In another embodiment, the desired values for one or more properties of the packed bed, the software system and the computer readable program code may be stored on the same memory medium.

Figure 5:
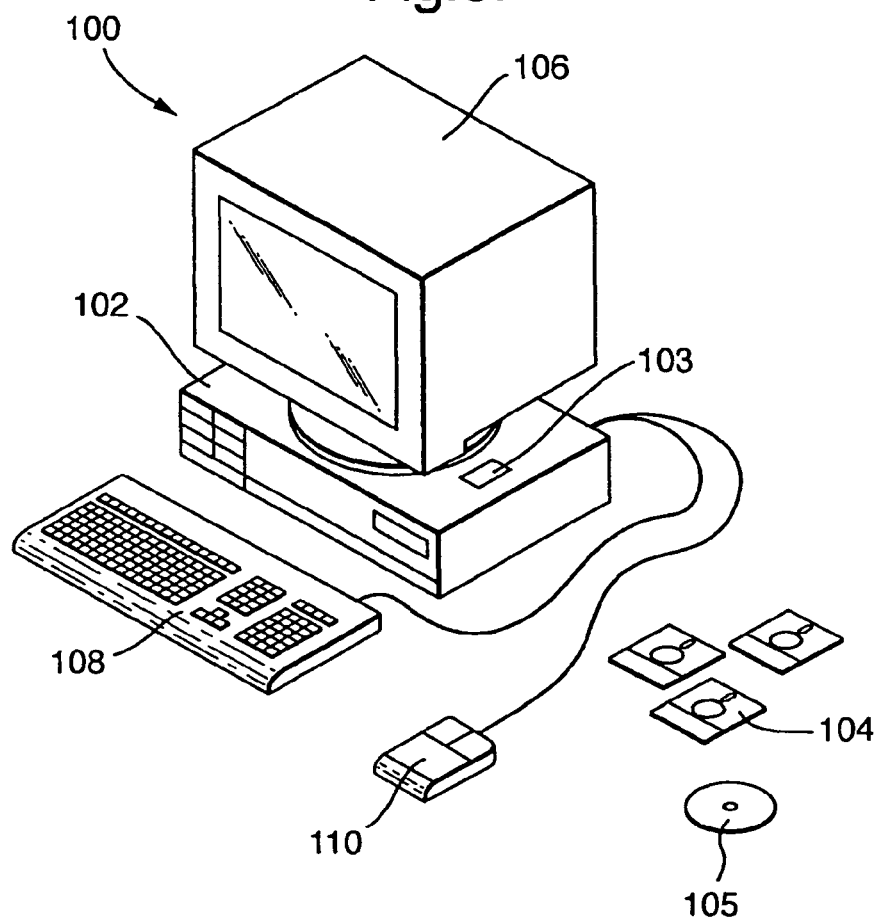
FIG. 5 is a schematic representation of a computer system in accordance with this invention.

As an illustration of a computer system suitable for use in the various embodiments of the processes of the present invention, FIG. 5 provides a schematic representation showing the computer system 100. Computer system 100 typically includes one or more central processing units 102 with associated computer program products 103, 104 and 105, represented by a computer system memory 103, floppy disks 104 or compact disk 105. Computer system 100 may further include one or more display devices, for example monitor 106, one or more alphanumeric input devices, for example keyboard 108, and/or one or more directional input devices, for example mouse 110.

We claim:

1. A process for selecting replacement shaped particles which are suitable for replacing shaped particles packed in an existing packed bed in a tube, wherein the process comprises:
    defining a desired value of a relative change in the pressure difference over the packed bed per unit length of the packed bed when the packed bed is subjected to conditions of a gas flowing through the packed bed, wherein the relative change results from the said replacement of the shaped particles by the replacement shaped particles,
    calculating dimensions of replacement shaped particles using a computer system having a central processing unit and a computer program such that a packed bed in the tube of the replacement shaped particles having the calculated dimensions exhibits a relative change in the pressure difference per unit length of the packed bed under the said conditions of gas flow which meets the desired value of the relative change in the pressure difference, and
    selecting the replacement shaped particles in accordance with the calculated dimensions, wherein the shaped particles of the existing packed bed are standard 8 mm cylinders, the replacement shaped particles have a cylinder geometric configuration, which may or may not be hollow, which is defined by a cylinder length, a cylinder diameter and a cylinder bore diameter, on the understanding that in the absence of a bore the cylinder bore diameter is deemed to be zero, and wherein the dimensions are calculated by using a relationship which can be defined by the following expression:

$$(\Delta P' - \Delta P_1)/\Delta P_1 = s + t \times (L/D_o) + u \times D_o + v \times D_i + w \times L + y \times D_t,$$

wherein $\Delta P'$ represents the pressure difference per unit length of the packed bed, $\Delta P_1$ represents the pressure difference per unit length of the existing packed bed, $(\Delta P' - \Delta P_1)/\Delta P_1$ represents the desired value of the relative change in the pressure difference per unit length of the packed bed, L represents the cylinder length, $D_o$ represents the cylinder diameter, $D_i$ represents the cylinder bore diameter, $D_t$ represents the diameter of the tube, and each of s, t, u, v, w, and y represents a constant having a dimension accommodating the dimension of the corresponding term of the expressions.

2. A process as claimed in claim 1, wherein
$(\Delta P' - \Delta P_1)/\Delta P_1$ is a dimensionless number,
L is expressed in mm,
$D_o$ is expressed in mm,
$D_i$ is expressed in mm,
$D_t$ is expressed in mm, and
the values of the constants s, t, u, v, w, and y are in the following ranges:
s from −5 to 20,
t from −20 to 5,
u from −2.5 to 0.5,
v from −0.4 to 0.2,
w from −1 to 2, and
y from −0.06 to 0.03.

3. A process as claimed in claim 1, wherein the values of the constants s, t, u, v, w, and y are in the following ranges:
s from 3 to 15,
t from −12 to 0,
u from −1.5 to 0,
v from −0.25 to 0.05,
w from −0.2 to 1.3, and
y from −0.035 to 0.01.

4. A process as claimed in claim 1, wherein the values of the constants s, t, u, v, w, and y are in the following ranges:
s from 6 to 12,
t from −8.8 to −3.1,
u from −1.1 to −0.4,
v from −0.18 to −0.03,
w from 0.19 to 0.91, and
y from −0.023 to −0.002.

5. A process for selecting shaped particles for use in a system which comprises a tube which is capable of being packed with shaped particles to form a packed bed in the tube, wherein the process comprises:
defining a desired value of one or more properties of the packed bed,
calculating dimensions of the shaped particles using a computer system having a central processing unit and a computer program such that a packed bed in the tube of the shaped particles having the calculated dimensions meets the desired value(s), and
selecting shaped particles in accordance with the calculated dimensions, wherein the said one or more properties of the packed bed comprise one or more of:
the volume fraction which is occupied by shaped particles,
the packing density, and
the resistivity for a gas flowing through the packed bed causing a pressure difference between a gas inlet and a gas outlet of the packed bed, which resistivity is defined by the expression:

$$\Delta P = R \times \rho \times V^2,$$

wherein $\Delta P$ represents the pressure difference per unit length of the packed bed, R represents the resistivity, $\rho$ represents the density of the gas and V represents the superficial gas velocity, wherein the density of the gas and the superficial gas velocity are as measured at the average value of gas inlet temperature and gas outlet temperature of the packed bed and the average value of gas inlet pressure and gas outlet pressure of the packed bed;
wherein the shaped particles have a cylinder geometric configuration, which may or may not be hollow, and which is defined by a cylinder length, a cylinder diameter and a cylinder bore diameter, on the understanding that in the absence of a bore the cylinder bore diameter is deemed to be zero; and
wherein dimensions are calculated using one or more relationships which can be defined by one or more of the following expressions:
when the property is the volume fraction which is occupied by shaped particles:

$$V_p = a + b \times (L/D_o) + c \times D_i + d \times D_o^2 + e \times D_t, \text{ or}$$

$$V_p = a' \times [(D_t/D_o)^2/(b' + (D_t/D_o)^2)] - c' \times [(D_t/D_o)^2],$$

and/or
when the property is the packing density:

$$PD = D_e \times [a + b \times (L/D_o) + c \times D_i + d \times D_o^2 + e \times D_i], \text{ or}$$

$$PD = D_e \times [a' \times [(D_t/D_o)^2/(b' + (D_t/D_o)^2)] - c' \times (D_t/D_o)^2]],$$

and/or
when the property is the resistivity:

$$R = 1 + m \times (L/D_o) + n \times D_o + p \times D_i + q \times L + r \times D_t,$$

wherein:
$V_p$ represents the desired value of the volume fraction of the packed bed which is occupied by shaped particles,
PD represents the desired value of the packing density,
R represents the desired value of the resistivity,
L represents the cylinder length,
$D_o$ represents the cylinder diameter,
$D_i$ represents the cylinder bore diameter,
$D_e$ represents the particle density,
$D_t$ represents the inside diameter of the tube, and
each of a, a', b, b', c, c', d, e, l, m, n, p, q and r represents a constant having a dimension accommodating the dimension of the corresponding term of the expressions.

6. A process as claimed in claim 5, wherein the said properties of the packed bed comprise (1) the volume fraction which is occupied by shaped particles or the packing density, and (2) the resistivity.

7. A process as claimed in claim 5, wherein
$V_p$ is a fraction of 1,
PD is expressed in kg/m3,
R is expressed in mm-1,
L is expressed in mm,
$D_o$ is expressed in mm,
$D_i$ is expressed in mm,
$D_e$ is expressed in kg/m3,
$D_t$ is expressed in mm, and
the values of the constants a, a', b, b' c, c', d, e, l, m, n, p, q and r are in the following ranges:
a from 0.2 to 0.7,
a' from 0.3 to 1 b from −0.2 to 0.1,
b' from −1 to 6
c from −0.05 to 0.01,
c' from 0.1 to 1.5
d from −0.001 to 0.0002,
e from 0.001 to 0.007,
l from −1 to 7,
m from −5 to 2,
n from −0.8 to 0,
p from −0.2 to 0.05,
q from −0.3 to 0.6, and
r from 0.01 to 0.07.

8. A process as claimed in claim 5, wherein the values of the constants a, a', b, b', c, c', d, e, l, m, n, p, q and r are in the following ranges:
a from 0.35 to 0.55,
a' from 0.5 to 0.8
b from −0.1 to 0.05,
b' from 1 to 4
c from −0.03 to −0.01,
c' from 0.5 to 0.85
d from −0.0007 to −0.0001,
e from 0.0025 to 0.0055,
l from 1.5 to 5,
m from −3.5 to 0,
n from −0.6 to −0.15,
p from −0.12 to −0.02,
q from −0.1 to 0.4, and
r from 0.03 to 0.05.

9. A process as claimed in claim 5, wherein the values of the constants a, a', b, b' c, c', d, e, l, m, n, p, q and r are in the following ranges:
a from 0.42 to 0.5,
a' from 0.62 to 0.68
b from −0.053 to 0.016,
b' from 1.7 to 3
c from −0.025 to −0.017,
c' from 0.59 to 0.77
d from −0.00055 to −0.00022,
e from 0.0032 to 0.0045,
l from 2.6 to 4.3,
m from −2.7 to −0.9,
n from −0.47 to −0.25,
p from −0.094 to −0.046,
q from 0.01 to 0.25, and
r from 0.035 to 0.042.

10. A process as claimed in claim 5, wherein the dimensions of the shaped particles are calculated by using a computer system.

* * * * *